US010085548B2

(12) United States Patent
Jimenez et al.

(10) Patent No.: US 10,085,548 B2
(45) Date of Patent: Oct. 2, 2018

(54) DISPENSER

(71) Applicant: Colgate-Palmolive Company, New York, NY (US)

(72) Inventors: Eduardo J. Jimenez, Manalapan, NJ (US); Joseph E. Fattori, East Sandwich, MA (US)

(73) Assignee: Colgate-Palmolive Company, New York, NY (US)

( * ) Notice: Subject to any disclaimer, the term of this patent is extended or adjusted under 35 U.S.C. 154(b) by 83 days.

(21) Appl. No.: 15/192,553

(22) Filed: Jun. 24, 2016

(65) Prior Publication Data

US 2016/0302562 A1 Oct. 20, 2016

Related U.S. Application Data

(63) Continuation of application No. 13/955,717, filed on Jul. 31, 2013, now Pat. No. 9,398,803, which is a
(Continued)

(51) Int. Cl.
*A45D 34/04* (2006.01)
*A45D 40/04* (2006.01)
(Continued)

(52) U.S. Cl.
CPC ............... *A46B 9/04* (2013.01); *A45D 34/04* (2013.01); *A45D 40/04* (2013.01); *A46B 5/0095* (2013.01); *A46B 5/021* (2013.01); *A46B 11/0024* (2013.01); *A46B 11/0027* (2013.01); *A46B 11/0034* (2013.01); *A46B 11/0065* (2013.01); *A61C 17/227* (2013.01);
(Continued)

(58) Field of Classification Search
CPC .................. A45D 34/04; A45D 40/04
USPC ....................................... 401/6, 265
See application file for complete search history.

(56) References Cited

U.S. PATENT DOCUMENTS

| 64,832 A | 5/1867 | Wylie |
| 261,456 A | 7/1882 | Hoffman |

(Continued)

FOREIGN PATENT DOCUMENTS

| CN | 201025977 | 2/2008 |
| DE | 2725495 | 12/1977 |

(Continued)

OTHER PUBLICATIONS

ISR and Written Opinion for PCT/US2009/069402 dated Jul. 23, 2010.

(Continued)

*Primary Examiner* — David Walczak
*Assistant Examiner* — Joshua Wiljanen

(57) ABSTRACT

A dispenser that includes a resilient applicator that optimizes application of a subject fluid to a desired surface. In one embodiment, the invention is a dispenser comprising a housing having an internal reservoir containing the fluid. The resilient applicator is coupled to the housing and comprises a dispensing orifice. The resilient applicator comprises a working surface that is oriented at an oblique angle to a longitudinal axis of the housing and is defined by a polygonal perimeter edge, the polygonal perimeter edge comprising a plurality of apex portions and a plurality of side portions, wherein one of the plurality of side portions forms a distal most-portion of the resilient applicator.

20 Claims, 7 Drawing Sheets

Related U.S. Application Data continuation of application No. 13/513,668, filed as application No. PCT/US2011/045010 on Jul. 22, 2011, now Pat. No. 8,523,475, which is a continuation of application No. PCT/US2010/060874, filed on Dec. 22, 2010, and a continuation of application No. PCT/US2009/069408, filed on Dec. 23, 2009, and a continuation of application No. PCT/US2009/069402, filed on Dec. 23, 2009, said application No. 13/513,668 is a continuation of application No. PCT/US2011/046132, filed on Aug. 1, 2011, which is a continuation of application No. PCT/US2010/060874, filed on Dec. 22, 2010, said application No. 13/513,668 is a continuation of application No. PCT/US2010/060867, filed on Dec. 16, 2010, and a continuation of application No. PCT/US2009/069408, filed on Dec. 23, 2009, and a continuation of application No. PCT/US2009/069402, filed on Dec. 23, 2009, said application No. 13/513,668 is a continuation of application No. PCT/US2010/060861, filed on Dec. 16, 2010, and a continuation of application No. PCT/US2009/069408, filed on Dec. 23, 2009, and a continuation of application No. PCT/US2009/069402, filed on Dec. 23, 2009, said application No. 13/513,668 is a continuation of application No. PCT/US2010/060877, filed on Dec. 16, 2010, and a continuation of application No. PCT/US2009/069408, filed on Dec. 23, 2009, and a continuation of application No. PCT/US2009/069402, filed on Dec. 23, 2009, said application No. 13/513,668 is a continuation of application No. PCT/US2010/060881, filed on Dec. 16, 2010, and a continuation of application No. PCT/US2009/069408, filed on Dec. 23, 2009, and a continuation of application No. PCT/US2009/069402, filed on Dec. 23, 2009, said application No. 13/513,668 is a continuation of application No. PCT/US2009/069408, filed on Dec. 23, 2009, and a continuation of application No. PCT/US2009/069402, filed on Dec. 23, 2009.

(60) Provisional application No. 61/423,414, filed on Dec. 15, 2010, provisional application No. 61/410,514, filed on Nov. 5, 2010, provisional application No. 61/423,397, filed on Dec. 15, 2010, provisional application No. 61/423,435, filed on Dec. 15, 2010, provisional application No. 61/423,449, filed on Dec. 15, 2010.

(51) Int. Cl.
*A46B 9/04* (2006.01)
*A46B 11/00* (2006.01)
*A61C 19/06* (2006.01)
*A46B 5/00* (2006.01)
*A46B 5/02* (2006.01)
*A61C 17/22* (2006.01)

(52) U.S. Cl.
CPC .... *A61C 19/066* (2013.01); *A46B 2200/1066* (2013.01); *Y10T 29/49826* (2015.01)

(56) References Cited

U.S. PATENT DOCUMENTS

| | | |
|---|---|---|
| 1,244,324 A | 10/1917 | Hackley |
| 1,292,416 A | 1/1919 | Auld |
| 1,546,516 A | 7/1925 | Smith |
| 1,555,064 A | 9/1925 | La Mothe |
| 1,668,511 A | 5/1928 | McLaughlin |
| 1,701,030 A | 2/1929 | Collins |
| 1,746,474 A | 2/1930 | Hogner |
| 1,913,528 A | 6/1933 | White |
| 1,975,723 A | 10/1934 | Johnssen |
| D134,723 S | 1/1943 | Riksheim |
| 2,356,874 A | 8/1944 | Nageotte |
| 2,437,769 A | 3/1948 | Traylor |
| 2,445,571 A | 7/1948 | Fuston |
| 2,448,033 A | 8/1948 | Kruck |
| 2,521,882 A | 9/1950 | Swift et al. |
| 2,541,949 A | 2/1951 | Thacker et al. |
| 2,579,899 A | 12/1951 | Burrows |
| 2,637,060 A | 5/1953 | Cowan |
| 2,670,881 A | 3/1954 | Sjoblorn |
| 2,676,568 A | 4/1954 | Maczynski |
| 2,718,299 A | 9/1955 | Atwater et al. |
| 2,771,858 A | 11/1956 | Cribbs et al. |
| 2,800,899 A | 7/1957 | Barron |
| 2,885,110 A | 5/1959 | Tregilgas |
| 2,885,116 A | 5/1959 | Tregilgas |
| 3,108,687 A | 10/1963 | Dayton |
| 3,148,684 A | 9/1964 | Keeler |
| 3,181,539 A | 5/1965 | Aston |
| 3,187,758 A | 6/1965 | Eklund |
| 3,215,320 A | 11/1965 | Heisler et al. |
| 3,293,749 A | 12/1966 | George et al. |
| 3,296,642 A | 1/1967 | Aylott |
| 3,358,699 A | 12/1967 | Bau |
| 3,359,991 A | 12/1967 | Spatz |
| 3,359,992 A | 12/1967 | Cishek et al. |
| 3,378,176 A | 4/1968 | Snyder |
| 3,406,694 A | 10/1968 | Odence |
| 3,468,612 A | 9/1969 | Aston |
| 3,683,924 A | 8/1972 | Louie |
| 3,910,706 A | 10/1975 | Del Bon |
| 3,986,645 A | 10/1976 | Baldwin et al. |
| 4,275,750 A | 6/1981 | Clark |
| 4,277,194 A | 7/1981 | Smith |
| 4,296,518 A | 10/1981 | Furrier et al. |
| 4,323,157 A | 4/1982 | Idec |
| 4,331,267 A | 5/1982 | Duncan et al. |
| 4,340,367 A | 7/1982 | Vadas et al. |
| 4,350,712 A | 9/1982 | Kocharian et al. |
| 4,384,645 A | 5/1983 | Manfredi |
| 4,413,760 A | 11/1983 | Paton |
| 4,506,810 A | 3/1985 | Goncalves |
| 4,527,574 A | 7/1985 | Manfredi |
| 4,573,820 A | 3/1986 | Kirchhoff |
| 4,582,059 A | 4/1986 | Tiwari |
| 4,641,766 A | 2/1987 | Vlasich |
| 4,655,372 A | 4/1987 | Ross et al. |
| 4,659,327 A | 4/1987 | Bennett et al. |
| 4,662,385 A | 5/1987 | Schefer |
| 4,763,815 A | 8/1988 | Von Schuckmann et al. |
| 4,767,032 A | 8/1988 | Smith |
| 4,776,717 A | 10/1988 | Iizuka et al. |
| 4,808,022 A | 2/1989 | Iizuka et al. |
| 4,826,341 A | 5/1989 | Kwak |
| 4,874,117 A | 10/1989 | Kay et al. |
| 4,879,781 A | 11/1989 | Desimone |
| 4,886,186 A | 12/1989 | Andris |
| 4,887,924 A | 12/1989 | Green |
| 4,892,427 A | 1/1990 | Ford |
| D310,308 S | 9/1990 | Wolsey |
| 4,954,000 A | 9/1990 | Gueret |
| 4,997,299 A | 3/1991 | Ohba |
| 5,000,356 A | 3/1991 | Johnson et al. |
| 5,011,317 A | 4/1991 | Gueret |
| 5,016,782 A | 5/1991 | Pfanstiel |
| 5,018,892 A | 5/1991 | Krueckel et al. |
| 5,066,155 A | 11/1991 | English et al. |
| 5,156,479 A | 10/1992 | Iizuka |
| 5,199,807 A | 4/1993 | Uchida |
| 5,217,475 A | 6/1993 | Kuber |
| 5,234,136 A | 8/1993 | Kopis |
| 5,249,876 A | 10/1993 | Hattman |
| 5,294,205 A | 3/1994 | Moeck et al. |

(56) References Cited

U.S. PATENT DOCUMENTS

| | | |
|---|---|---|
| 5,336,005 A | 8/1994 | Moeck et al. |
| 5,423,623 A | 6/1995 | Bakic |
| 5,454,660 A | 10/1995 | Sakurai et al. |
| 5,540,361 A | 7/1996 | Fattori |
| 5,547,302 A | 8/1996 | Dornbusch et al. |
| 5,560,518 A | 10/1996 | Catterall et al. |
| 5,569,278 A | 10/1996 | Persad |
| 5,573,341 A | 11/1996 | Iaia |
| 5,697,531 A | 12/1997 | Fattori |
| 5,709,004 A | 1/1998 | Paduano et al. |
| 5,725,133 A | 3/1998 | Iaia |
| 5,733,058 A | 3/1998 | Hofmann |
| 5,765,573 A | 6/1998 | Gueret |
| 5,772,347 A | 6/1998 | Gueret |
| 5,791,801 A | 8/1998 | Miller |
| 5,803,640 A | 9/1998 | Nakajima et al. |
| 5,827,002 A | 10/1998 | Nakajima |
| 5,827,308 A | 10/1998 | Thakur et al. |
| 5,839,622 A | 11/1998 | Bicknell et al. |
| 5,851,079 A | 12/1998 | Horstman et al. |
| 5,860,572 A | 1/1999 | Harrold et al. |
| 5,879,095 A | 3/1999 | Gueret |
| 5,893,860 A | 4/1999 | Ripich et al. |
| 5,916,228 A | 6/1999 | Ripich et al. |
| 5,941,254 A | 8/1999 | Heler |
| 5,955,114 A | 9/1999 | Llanos |
| 5,996,850 A | 12/1999 | Morali et al. |
| 6,015,293 A | 1/2000 | Rimkus |
| 6,039,053 A | 3/2000 | Turrentine |
| 6,056,763 A | 5/2000 | Parsons |
| 6,070,598 A | 6/2000 | Gueret |
| 6,071,026 A | 6/2000 | Martinez et al. |
| 6,082,918 A | 7/2000 | Gueret |
| 6,086,276 A | 7/2000 | Gueret |
| 6,200,055 B1 | 3/2001 | Fusaro, Jr. |
| 6,202,247 B1 | 3/2001 | Lorenz, Jr. |
| 6,210,061 B1 | 4/2001 | Johnson |
| 6,213,662 B1 | 4/2001 | Aljanedi |
| 6,220,773 B1 | 4/2001 | Wiegner et al. |
| 6,224,573 B1 | 5/2001 | Yeager et al. |
| 6,227,209 B1 | 5/2001 | Kim et al. |
| 6,238,117 B1 | 5/2001 | Griebel et al. |
| 6,290,417 B1 | 9/2001 | Kaminski |
| 6,325,076 B1 | 12/2001 | Ramirez |
| 6,331,085 B1 | 12/2001 | Schrepf et al. |
| 6,345,629 B1 | 2/2002 | Vives |
| 6,363,949 B1 | 4/2002 | Brown |
| 6,368,001 B1 | 4/2002 | Roeder |
| 6,398,439 B1 | 6/2002 | Szekely |
| 6,406,694 B1 | 6/2002 | LaRosa |
| 6,440,149 B1 | 8/2002 | Potti |
| 6,450,716 B1 | 9/2002 | Szekely |
| 6,475,172 B1 | 11/2002 | Hall |
| 6,488,427 B1 | 12/2002 | Breidenbach et al. |
| 6,592,281 B2 | 7/2003 | Clark et al. |
| 6,607,323 B2 | 8/2003 | Breidenbach et al. |
| 6,647,581 B1 | 11/2003 | Persad et al. |
| 6,672,783 B1 | 1/2004 | Licata et al. |
| 6,688,317 B2 | 2/2004 | Gueret |
| 6,688,793 B2 | 2/2004 | Goyet |
| 6,688,796 B1 | 2/2004 | Lin |
| 6,745,781 B2 | 6/2004 | Gueret |
| 6,746,170 B2 | 6/2004 | Delage |
| 6,752,558 B2 | 6/2004 | Hsu |
| 6,824,018 B1 | 11/2004 | Eaddy et al. |
| 6,866,438 B2 | 3/2005 | Bauer et al. |
| 6,880,999 B2 | 4/2005 | Biegel et al. |
| 6,918,511 B1 | 7/2005 | Spatz et al. |
| 6,923,587 B2 | 8/2005 | Lee |
| 6,957,753 B2 | 10/2005 | Tani |
| 7,029,484 B2 | 4/2006 | Ripich |
| 7,044,671 B2 | 5/2006 | Parikh et al. |
| 7,051,642 B2 | 5/2006 | Kageyama |
| 7,055,527 B2 | 6/2006 | Tien |
| 7,086,564 B1 | 8/2006 | Corrigan |
| 7,086,796 B2 | 8/2006 | Severa |
| 7,089,564 B2 | 8/2006 | Chen et al. |
| 7,114,505 B2 | 10/2006 | Bauer et al. |
| 7,143,462 B2 | 12/2006 | Hohlbein |
| 7,144,175 B2 | 12/2006 | Biegel |
| 7,168,435 B2 | 1/2007 | Vieu et al. |
| 7,192,212 B2 | 3/2007 | Gutberlet et al. |
| 7,201,527 B2 | 4/2007 | Thorpe et al. |
| 7,210,870 B2 | 5/2007 | Breidenbach et al. |
| 7,217,054 B2 | 5/2007 | Noguchi |
| 7,226,231 B2 | 6/2007 | Py et al. |
| 7,237,974 B2 | 7/2007 | Pfenniger et al. |
| 7,237,975 B2 | 7/2007 | Noguchi |
| 7,303,348 B2 | 12/2007 | Phipps et al. |
| 7,309,184 B2 | 12/2007 | Butcher et al. |
| 7,309,185 B2 | 12/2007 | Thorpe et al. |
| 7,347,360 B2 | 3/2008 | Lasch et al. |
| 7,374,360 B1 | 5/2008 | Szekely |
| 7,396,180 B2 | 7/2008 | Bugla et al. |
| 7,401,373 B2 | 7/2008 | Tybinkowski et al. |
| 7,461,988 B2 | 12/2008 | Albisetti |
| 7,465,113 B2 | 12/2008 | Gueret |
| 7,474,048 B2 | 1/2009 | Forrest et al. |
| 7,481,591 B2 | 1/2009 | Dumler |
| 7,520,406 B2 | 4/2009 | Jaichandra et al. |
| 7,557,936 B2 | 7/2009 | Dickinson |
| 7,614,811 B2 | 11/2009 | Kaufman et al. |
| 7,641,411 B2 | 1/2010 | Biegel |
| 7,651,291 B2 | 1/2010 | Py et al. |
| 7,665,923 B2 | 2/2010 | Py et al. |
| 7,823,593 B2 | 11/2010 | Gueret |
| 2002/0054783 A1 | 5/2002 | Gueret |
| 2002/0073496 A1 | 6/2002 | Kim |
| 2003/0057236 A1 | 3/2003 | Delage |
| 2004/0028456 A1 | 2/2004 | Giraldo |
| 2004/0092981 A1 | 5/2004 | Barlow et al. |
| 2004/0237996 A1 | 12/2004 | Fischer et al. |
| 2004/0240928 A1 | 12/2004 | Trocino |
| 2005/0006409 A1 | 1/2005 | Ganzeboom |
| 2005/0026774 A1 | 2/2005 | Nolan |
| 2005/0069372 A1 | 3/2005 | Hohlbein et al. |
| 2005/0199655 A1 | 9/2005 | Petit |
| 2006/0058821 A1 | 3/2006 | Jansheski |
| 2006/0207627 A1 | 9/2006 | Thorpe et al. |
| 2006/0233588 A1 | 10/2006 | Gueret |
| 2006/0269354 A1 | 11/2006 | Lane |
| 2006/0272666 A1 | 12/2006 | Wyatt et al. |
| 2006/0275225 A1 | 12/2006 | Prencipe et al. |
| 2007/0007302 A1 | 1/2007 | Jaichandra et al. |
| 2007/0079845 A1 | 4/2007 | Gueret |
| 2007/0227553 A1 | 10/2007 | Gueret |
| 2007/0231055 A1 | 10/2007 | Albisetti |
| 2007/0292194 A1 | 12/2007 | Albisetti et al. |
| 2008/0063464 A1 | 3/2008 | Prague |
| 2008/0089733 A1 | 4/2008 | Lochak |
| 2008/0101850 A1 | 5/2008 | Wojcik et al. |
| 2008/0189888 A1 | 8/2008 | Hohlbein |
| 2008/0274066 A1 | 11/2008 | Montgomery |
| 2009/0074679 A1 | 3/2009 | Silverman |
| 2009/0254055 A1 | 10/2009 | Clarke |
| 2009/0261007 A1 | 10/2009 | Sanchez |
| 2009/0317432 A1 | 12/2009 | Kergosien |
| 2010/0168638 A1 | 7/2010 | Korogi et al. |
| 2010/0240013 A1 | 9/2010 | Levine |
| 2011/0308030 A1 | 12/2011 | Jimenez et al. |
| 2012/0114410 A1 | 5/2012 | Jimenez et al. |
| 2012/0163902 A1 | 5/2012 | Jimenez et al. |

FOREIGN PATENT DOCUMENTS

| | | |
|---|---|---|
| DE | 3832224 | 8/1989 |
| DE | 29613012 | 10/1996 |
| EP | 1506726 | 2/2005 |
| FR | 850458 | 12/1939 |
| FR | 907669 | 3/1946 |
| FR | 1596074 | 6/1970 |
| FR | 2597734 | 10/1987 |
| GB | 666082 | 2/1952 |
| GB | 2085717 | 5/1982 |

(56) References Cited

FOREIGN PATENT DOCUMENTS

| | | |
|---|---|---|
| GB | 2280361 | 2/1995 |
| JP | 48-093167 | 12/1973 |
| NL | 2002311 | 6/2010 |
| WO | WO 93/03648 | 3/1993 |
| WO | WO 98/009572 | 3/1998 |
| WO | WO 98/018695 | 5/1998 |
| WO | WO 01/000103 | 1/2001 |
| WO | WO 02/017967 | 3/2002 |
| WO | WO 04/112637 | 12/2004 |
| WO | WO 08/062935 | 5/2008 |
| WO | WO 09/151455 | 12/2009 |
| WO | WO 11/078863 | 6/2011 |
| WO | WO 11/078864 | 6/2011 |
| WO | WO 11/079027 | 6/2011 |
| WO | WO 11/079028 | 6/2011 |
| WO | WO 12/082102 | 6/2012 |
| WO | WO 12/082185 | 6/2012 |

OTHER PUBLICATIONS

Written Opinion for PCT/US2009/069402 dated Dec. 16, 2011.
ISR and Written Opinion for PCT/US2009/069408 dated Jul. 23, 2010.
Written Opinion for PCT/US2009/069408 dated Dec. 16, 2011.
ISR and Written Opinion for PCT/US2010/049102 dated Jun. 7, 2011.
ISR and Written Opinion for PCT/US2010/060105 dated Aug. 30, 2011.
ISR and Written Opinion for PCT/US2010/060861 dated Jun. 8, 2011.
ISR and Written Opinion for PCT/US2010/060867 dated Oct. 14, 2011.
ISR and Written Opinion for PCT/US2010/060874 dated Jan. 11, 2012.
ISR and Written Opinion for PCT/US2010/060877 dated Oct. 7, 2011.
ISR and Written Opinion for PCT/US2010/060881 dated May 16, 2011.
Written Opinion for PCT/US2010/060881 dated Dec. 28, 2011.
ISR and Written Opinion for PCT/US2011/023356 dated Oct. 21, 2011.
ISR and Written Opinion for PCT/US2011/045010 dated Nov. 25, 2011.
ISR and Written Opinion for PCT/US2011/046132 dated Dec. 1, 2011.

DISPENSER

CROSS-REFERENCE TO RELATED APPLICATIONS

This application is a continuation of U.S. patent application Ser. No. 13/955,717, filed on Jul. 31, 2013, which is a continuation of U.S. patent application Ser. No. 13/513,668, filed on Jun. 4, 2012, which is a U.S. national stage entry under 35 U.S.C. § 371 of Patent Cooperation Treaty Patent Application No. PCT/US2011/045010, filed Jul. 22, 2011, which in turn claims priority to Patent Cooperation Treaty Patent Application No. PCT/US10/60874, filed on Dec. 22, 2010, which in turn claims the benefit of U.S. Provisional Patent Application No. 61/423,414, filed on Dec. 15, 2010; U.S. Provisional Patent Application No. 61/410,514, filed on Nov. 5, 2010; U.S. Provisional Patent Application No. 61/423,397, filed on Dec. 15, 2010; U.S. Provisional Patent Application No. 61/423,435 filed on Dec. 15, 2010; U.S. Provisional Patent Application No. 61/423,449, filed on Dec. 15, 2010; Patent Cooperation Treaty Patent Application No. PCT/US2009/069408, filed on Dec. 23, 2009; and Patent Cooperation Treaty Patent Application No. PCT/US2009/069402, filed on Dec. 23, 2009.

Further, this application claims the benefit of Patent Cooperation Treaty Patent Application No. PCT/US2011/046132, filed on Aug. 1, 2011, which in turn claims the benefit of Patent Cooperation Treaty Patent Application No. PCT/US2010/060874, filed on Dec. 22, 2010 and U.S. Provisional Patent Application No. 61/423,414, filed on Dec. 15, 2010.

Additionally, this application claims the benefit of Patent Cooperation Treaty Patent Application No. PCT/US2010/060867, filed on Dec. 16, 2010, which in turn claims the benefit of U.S. Provisional Patent Application No. 61/423,414, filed on Dec. 15, 2010; U.S. Provisional Patent Application No. 61/410,514, filed on Nov. 5, 2010; U.S. Provisional Patent Application No. 61/423,397, filed on Dec. 15, 2010; U.S. Provisional Patent Application No. 61/423,435 filed on Dec. 15, 2010; U.S. Provisional Patent Application No. 61/423,449, filed on Dec. 15, 2010; Patent Cooperation Treaty Patent Application No. PCT/US2009/069408, filed on Dec. 23, 2009; and Patent Cooperation Treaty Patent Application No. PCT/US2009/069402, filed on Dec. 23, 2009.

Further, this application claims the benefit of Patent Cooperation Treaty Patent Application No. PCT/US2010/060861, filed on Dec. 16, 2010, which in turn claims the benefit of U.S. Provisional Patent Application No. 61/423,414, filed on Dec. 15, 2010; U.S. Provisional Patent Application No. 61/410,514, filed on Nov. 5, 2010; U.S. Provisional Patent Application No. 61/423,397, filed on Dec. 15, 2010; U.S. Provisional Patent Application No. 61/423,435 filed on Dec. 15, 2010; U.S. Provisional Patent Application No. 61/423,449, filed on Dec. 15, 2010; Patent Cooperation Treaty Patent Application No. PCT/US2009/069408, filed on Dec. 23, 2009; and Patent Cooperation Treaty Patent Application No. PCT/US2009/069402, filed on Dec. 23, 2009.

In addition, this application claims the benefit of Patent Cooperation Treaty Patent Application No. PCT/US2010/060877, filed on Dec. 16, 2010, which in turn claims the benefit of U.S. Provisional Patent Application No. 61/423,414, filed on Dec. 15, 2010; U.S. Provisional Patent Application No. 61/410,514, filed on Nov. 5, 2010; U.S. Provisional Patent Application No. 61/423,397, filed on Dec. 15, 2010; U.S. Provisional Patent Application No. 61/423,435 filed on Dec. 15, 2010; U.S. Provisional Patent Application No. 61/423,449, filed on Dec. 15, 2010; Patent Cooperation Treaty Patent Application No. PCT/US2009/069408, filed on Dec. 23, 2009; and Patent Cooperation Treaty Patent Application No. PCT/US2009/069402, filed on Dec. 23, 2009.

Further, this application claims the benefit of Patent Cooperation Treaty Patent Application No. PCT/US2010/060881, filed on Dec. 16, 2010, which in turn claims the benefit of U.S. Provisional Patent Application No. 61/423,414, filed on Dec. 15, 2010; U.S. Provisional Patent Application No. 61/410,514, filed on Nov. 5, 2010; U.S. Provisional Patent Application No. 61/423,397, filed on Dec. 15, 2010; U.S. Provisional Patent Application No. 61/423,435 filed on Dec. 15, 2010; U.S. Provisional Patent Application No. 61/423,449, filed on Dec. 15, 2010; Patent Cooperation Treaty Patent Application No. PCT/US2009/069408, filed on Dec. 23, 2009; and Patent Cooperation Treaty Patent Application No. PCT/US2009/069402, filed on Dec. 23, 2009.

Additionally, this application claims the benefit of Patent Cooperation Treaty Patent Application No. PCT/US2009/069408, filed on Dec. 23, 2009 and Patent Cooperation Treaty Patent Application No. PCT/US2009/069402, filed on Dec. 23, 2009.

The disclosures of the above applications are incorporated herein by reference.

BACKGROUND OF THE INVENTION

Oral care products or agents are applied in different ways. For example, without limitation, a common technique used for tooth whitening products is to cast an impression of a person's teeth and provide a tray of the shape of this impression. A person then only needs to add a whitening composition to the tray and to apply the tray to his/her teeth. This is left in place for a period of time and then removed. After a few treatments the teeth gradually whiten. Another technique is to use a strip that has a whitening composition on one surface. This strip is applied to a person's teeth and left in place for about 30 minutes. After several applications the teeth are gradually whitened. Yet another technique is to apply a whitening composition to teeth using a small brush. This brush is repeatedly dipped back into the container during the application of the tooth whitening composition to one's teeth. After a few treatments the teeth gradually whiten.

A problem with existing brushing techniques is that saliva in the mouth contains the enzyme catalase. This enzyme will catalyze the decomposition of peroxides. The brush can pick up some catalase during the application of some of the whitening product to teeth and transport that catalase back to the bottle. This catalase now in the bottle can degrade the peroxide in the bottle. Another problem with this latter technique is that it does not adapt for use with anhydrous whitening compositions. Here the brush may transport moisture from saliva from the mouth back into the bottle. This will have a negative effect on the whitening composition by potentially decomposing the peroxide active ingredient. In addition, if a person washes the brush each time after use, moisture from the wet bristles can enter the bottle.

While tray-based systems are suitable, many people do not use them due to the fact that they tend to be uncomfortable and/or awkward. Moreover, in order to use a whitening tray, a user must keep the tray and the required components at hand. This not only requires extra storage space in already cramped bathroom cabinets but also requires that the user remember to use the whitening system. Furthermore, these tray-based systems are not conveniently portable for transport and/or travel.

In addition to difficulties in applying some oral care products, storage is sometimes cumbersome and inconvenient for the user. The oral care product must typically be stored separately from oral care tooth cleaning implements such as a toothbrush since the oral care product package and toothbrush heretofore are generally treated as separate and distinct parts of an oral care regimen.

A more portable, compact and convenient way to store oral care products, and to dispense and apply those oral care products to oral surfaces is desired.

BRIEF SUMMARY OF THE INVENTION

Embodiments of the present invention provide a dispenser having an improved design for applying and spreading a fluid onto a desired surface. Advantageously, such embodiments are especially suited for easy transport and/or travel.

In one embodiment, the invention can be a dispenser comprising: a housing having an internal reservoir containing a fluid, the housing extending from a proximal end to a distal end along a longitudinal axis, the distal end of the housing comprising a transverse end wall having a top surface; a resilient applicator coupled to the distal end of the housing, the resilient applicator comprising a main body portion and a dispensing orifice for dispensing the fluid from the reservoir, the main body portion having a bottom surface that is in contact with the top surface of the transverse end wall of the housing; and wherein the resilient applicator comprises a working surface that is oriented at an oblique angle to the longitudinal axis of the housing In another embodiment, the invention can be a dispenser comprising: a housing having an internal reservoir containing a fluid, the housing extending from a proximal end to a distal end along a longitudinal axis; a resilient applicator coupled to the distal end of the housing, the resilient applicator comprising a main body portion having a working surface and a bottom surface and a dispensing orifice for dispensing the fluid from the reservoir, the dispensing orifice forming a fluid passageway from the bottom surface to the working surface, the fluid passageway having a transverse cross-sectional area that tapers from the working surface to the bottom surface; and wherein the working surface is oriented at an oblique angle to the longitudinal axis of the housing.

In yet another embodiment, the invention can be a dispenser comprising: a housing having an internal reservoir containing a fluid, the housing extending from a proximal end to a distal end along a longitudinal axis; and an applicator coupled to the distal end of the housing, the applicator comprising a main body portion having an outer peripheral surface and an inner surface that defines a dispensing orifice for dispensing the fluid from the reservoir, wherein the main body portion has a thickness measured from the outer peripheral surface to the inner surface along a reference plane that is substantially perpendicular to the longitudinal axis, and wherein the dispensing orifice has a width measured along the reference plane, the thickness of the main body portion being greater than the width of the dispensing orifice.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The features of the exemplified embodiments will be described with reference to the following drawings in which like elements are labeled similarly.

The present invention will become more fully understood from the detailed description and the accompanying drawings, wherein.

DETAILED DESCRIPTION OF THE INVENTION

Figure 1:
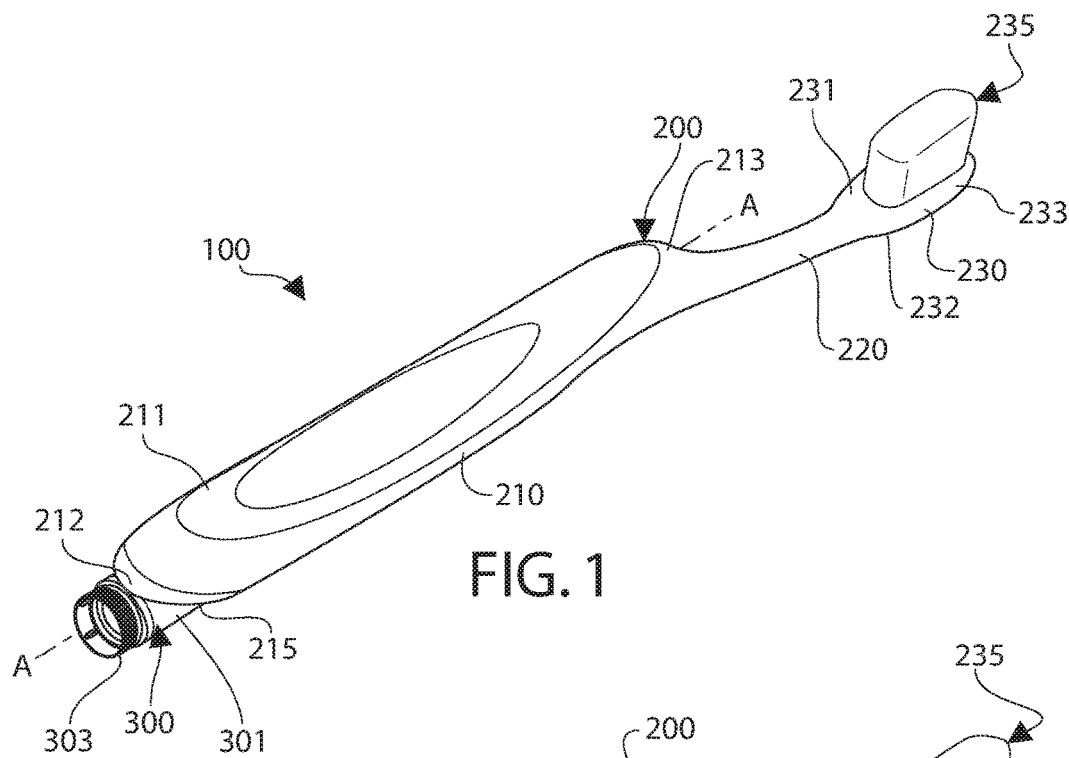
FIG. 1 is a front perspective view of an oral care system including a toothbrush and a dispenser according to one embodiment of the present invention, wherein the dispenser is coupled to the toothbrush.

The following description of the preferred embodiment(s) is merely exemplary in nature and is in no way intended to limit the invention, its application, or uses.

The description of illustrative embodiments according to principles of the present invention is intended to be read in connection with the accompanying drawings, which are to be considered part of the entire written description. In the description of embodiments of the invention disclosed herein, any reference to direction or orientation is merely intended for convenience of description and is not intended in any way to limit the scope of the present invention. Relative terms such as "lower," "upper," "horizontal," "vertical," "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such. Terms such as "attached," "affixed," "connected," "coupled," "interconnected," and similar refer to a relationship wherein structures are secured or attached to one another either directly or indirectly through intervening structures, as well as both movable or rigid attachments or relationships, unless expressly described otherwise. Moreover, the features and benefits of the invention are illustrated by reference to the exemplified embodiments. Accordingly, the invention expressly should not be limited to such exemplary embodiments illustrating some possible non-limiting combination of features that may exist alone or in other combinations of features; the scope of the invention being defined by the claims appended hereto.

Exemplary embodiments of the present invention will now be described with respect to one possible oral care or treatment system. Embodiments of the oral care system may include without limitation the following fluids such as fluidic oral care materials including: tooth whitening, anti-bacterial, enamel protection, anti-sensitivity, anti-inflammatory, anti-attachment, fluoride, tartar control/protection, flavorant, sensate, colorant and others. However, other embodiments of the present invention may be used to store and dispense any suitable type of fluid and the invention is expressly not limited to any particular oral care system or oral care material alone.

Figure 2:
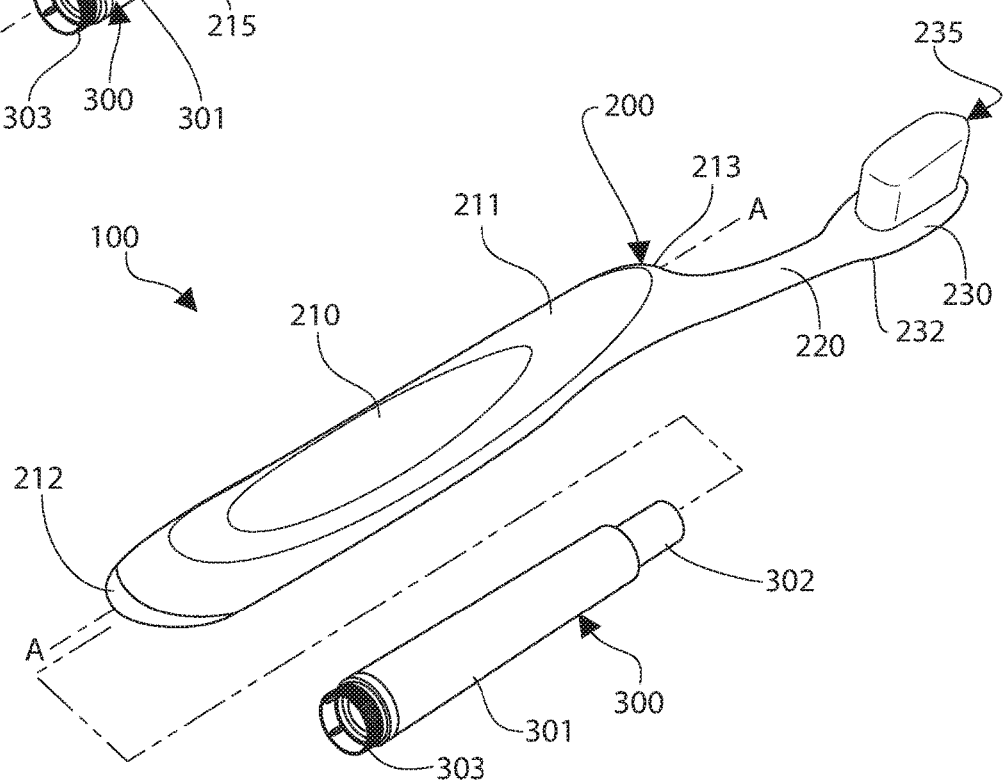
FIG. 2 is a front perspective view of the oral care system of FIG. 1 wherein the dispenser is removed from the toothbrush.

Referring to FIGS. 1-2, an oral care system 100 is illustrated according to one embodiment of the present invention. The oral care system 100 is a compact readily portable self-contained user-friendly system that comprises all of the necessary components and chemistries necessary for a user to perform a desired oral care treatment routine. As will be described in greater detail below, the oral care system 100 in one exemplary embodiment generally takes the form of a modified toothbrush having a detachable dispenser 300 disposed at least partially within its handle. Because the dispenser 300 is located within the handle of the toothbrush itself, the oral care system 100 is portable for travel, easy to use, and reduces the amount of required storage space. Furthermore, since the toothbrush 200 and dispenser 300 are housed together, the user is less likely to misplace the dispenser 300 and more inclined to maintain the oral treatment routine with the dispenser 300 since brushing will remind the user to simply detach and apply the contents of the dispenser 300.

However, it should be understood that the toothbrush 200 is not required in all embodiments of the present invention. In certain embodiments, the oral care dispenser 300 itself can be provided without the toothbrush 200. Thus, although the discussion below is directed mainly to the oral care system 100, which comprises both the toothbrush 200 and the dispenser 300, the invention is not to be so limited and the dispenser 300 can be sold, used and stored separate from the toothbrush 200, or alternatively as a kit with another toothbrush or oral care implement.

The oral care system 100 generally comprises a toothbrush body 200 (hereinafter referred to simply as a toothbrush) and a dispenser 300. While the invention is described herein with respect to the use of a toothbrush as one of the two primary components of the oral care system 100, it is to be understood that other alternate oral care implements can be used within the scope of the invention, including tongue cleaners, tooth polishers and specially designed ansate implements having tooth engaging elements. Additionally, as discussed above, in certain other embodiments the toothbrush 200 (or any alternate oral care implement) can be omitted altogether or simply packaged as a kit.

In certain instances, the toothbrush 200 may include tooth engaging elements that are specifically designed to increase the effect of the fluid in the dispenser 300 on the desired oral surface, such as the teeth, tongue, cheeks, gums or other soft tissue. For example, the tooth engaging elements may include elastomeric wiping elements that assist in removing stains from teeth and/or assist with forcing the fluid into the tubules of the teeth. Moreover, while the toothbrush 200 is exemplified as a manual toothbrush, the toothbrush may be a powered toothbrush in other embodiments of the invention. It is to be understood that the inventive system can be utilized for a variety of intended oral care needs by filling the dispenser 300 with the appropriate fluid, such as active or inactive oral care agents that achieve a desired oral effect, such as tooth anti-sensitivity agents, tooth whitening agents, medicaments, breath freshening agents, or combinations thereof. In one embodiment, the fluid is free of (i.e., is not) toothpaste as the dispenser 300 is intended to augment not supplant the brushing regimen. The fluid can be selected to complement a toothpaste formula, such as by coordinating flavors, colors, aesthetics, or active ingredients.

The toothbrush 200 generally comprises a handle 210, a neck 220 and a head 230. The handle 210 provides the user with a mechanism by which he/she can readily grip and manipulate the toothbrush 200. The handle 210 may be formed of many different shapes, sizes, materials and a variety of manufacturing methods that are well-known to those skilled in the art, so long as it can house the dispenser 300 therein as described in detail below. If desired, the handle 210 may include a suitable textured grip 211 made of soft elastomeric material. The handle 210 can be a single or multi-part construction. The handle 210 extends from a proximal end 212 to a distal end 213 along a longitudinal axis A-A. A cavity (not visible) is formed within the handle 210. An opening 215 is provided at the proximal end 212 of the handle 210 that provides a passageway into the cavity through which the dispenser 300 can be inserted and retracted. While the opening 215 is located at the proximal end 212 of the handle 210 in the exemplified embodiment, the opening 215 may be located at other positions on the handle 210 in other embodiments of the invention. For example, the opening 215 may be located on a longitudinal surface of the handle 210 (e.g., the front surface, the rear surface and/or the side surfaces) and be elongated to provide sufficient access to the cavity.

The handle 210 transitions into the neck 220 at the distal end 213. While the neck 220 generally has a smaller transverse cross-sectional area than the handle 210, the invention is not so limited. Broadly speaking, the neck 220 is merely the transition region between the handle 210 and the head 230 and can conceptually be considered as a portion of the handle 210. In this manner, the head 230 is connected to the distal end 213 of the handle 210 (via the neck 220).

The housing 301 is an elongated hollow tubular structure extending along the longitudinal axis B-B from a proximal end 315 to a distal end 316. The distal end 316 of the housing 301 comprises a transverse end wall 390 having a top surface 391. In the exemplified embodiment, the housing 301 has a generally circular transverse cross-sectional profile. However, the invention is not to be so limited and in certain other embodiments the housing 301 can have a non-circular transverse cross-sectional profile. The housing 301 is in the form of an elongated tubular barrel that extends along a central axis that is coaxial with the longitudinal axis B-B.

The head 230 generally comprises a front surface 231, a rear surface 232 and a peripheral side surface 233 that extends between the front and rear surfaces 231, 232. The front surface 231 and the rear surface 232 of the head 230 can take on a wide variety of shapes and contours, none of which are limiting of the present invention. For example, the front and rear surfaces 231, 232 can be planar, contoured or combinations thereof. Moreover, if desired, the rear surface 232 may also comprise additional structures for oral cleaning or tooth engagement, such as a soft tissue cleaner or a tooth polishing structure. An example of a soft tissue cleaner is an elastomeric pad comprising a plurality of nubs and or ridges. An example of a tooth polishing structure can be an elastomeric element, such as a prophy cup(s) or elastomeric wipers. Furthermore, while the head 230 is normally widened relative to the neck 220 of the handle 210, it could in some constructions simply be a continuous extension or narrowing of the handle 210.

The front surface 231 of the head 230 comprises a collection of oral cleaning elements such as tooth engaging elements 235 extending therefrom for cleaning and/or polishing contact with an oral surface and/or interdental spaces. While the collection of tooth engaging elements 235 is suited for brushing teeth, the collection of cleaning elements 235 can also be used to polish teeth instead of or in addition to cleaning teeth. As used herein, the term "tooth engaging elements" is used in a generic sense to refer to any structure that can be used to clean, polish or wipe the teeth and/or soft oral tissue (e.g. tongue, cheek, gums, etc.) through relative surface contact. Common examples of "tooth engaging elements" include, without limitation, bristle tufts, filament bristles, fiber bristles, nylon bristles, spiral bristles, rubber bristles, elastomeric protrusions, flexible polymer protrusions, combinations thereof and/or structures containing such materials or combinations. Suitable elastomeric materials include any biocompatible resilient material suitable for uses in an oral hygiene apparatus. To provide optimum comfort as well as cleaning benefits, the elastomeric material of the tooth or soft tissue engaging elements has a hardness property in the range of A8 to A25 Shore hardness. One suitable elastomeric material is styrene-ethylene/butylene-styrene block copolymer (SEBS) manufactured by GLS Corporation. Nevertheless, SEBS material from other manufacturers or other materials within and outside the noted hardness range could be used.

The tooth engaging elements 235 of the present invention can be connected to the head 230 in any manner known in the art. For example, staples/anchors, in-mold tufting (IMT) or anchor free tufting (AFT) could be used to mount the cleaning elements/tooth engaging elements. In AFT, a plate or membrane is secured to the brush head such as by ultrasonic welding. The bristles extend through the plate or membrane. The free ends of the bristles on one side of the plate or membrane perform the cleaning function. The ends of the bristles on the other side of the plate or membrane are melted together by heat to be anchored in place. Any suitable form of cleaning elements may be used in the broad practice of this invention. Alternatively, the bristles could be mounted to tuft blocks or sections by extending through suitable openings in the tuft blocks so that the base of the bristles is mounted within or below the tuft block.

The toothbrush 200 and the dispenser 300 are non-unitary separate structures that are specially designed in certain embodiments to be non-fixedly secured together when in an assembled state (referred to herein as a storage state) and completely isolated and separated from one another when in a disassembled state (referred to herein as an application state). Of course, as discussed above in certain embodiments the dispenser 300 is a stand-alone product that is not designed or intended to be housed within the toothbrush 200. The toothbrush 200 and the dispenser 300 are illustrated in the storage state in FIG. 1 and in the application state in FIG. 2. The dispenser 300 can be slidably manipulated and moved between the storage state (FIG. 1) in which the dispenser 300 is docked in the toothbrush handle portion 210 and the application state (FIG. 2) in which the dispenser 300 is removed from the handle portion 210 by the user as desired. The dispenser 300 will now be described in greater detail.

Figure 3:
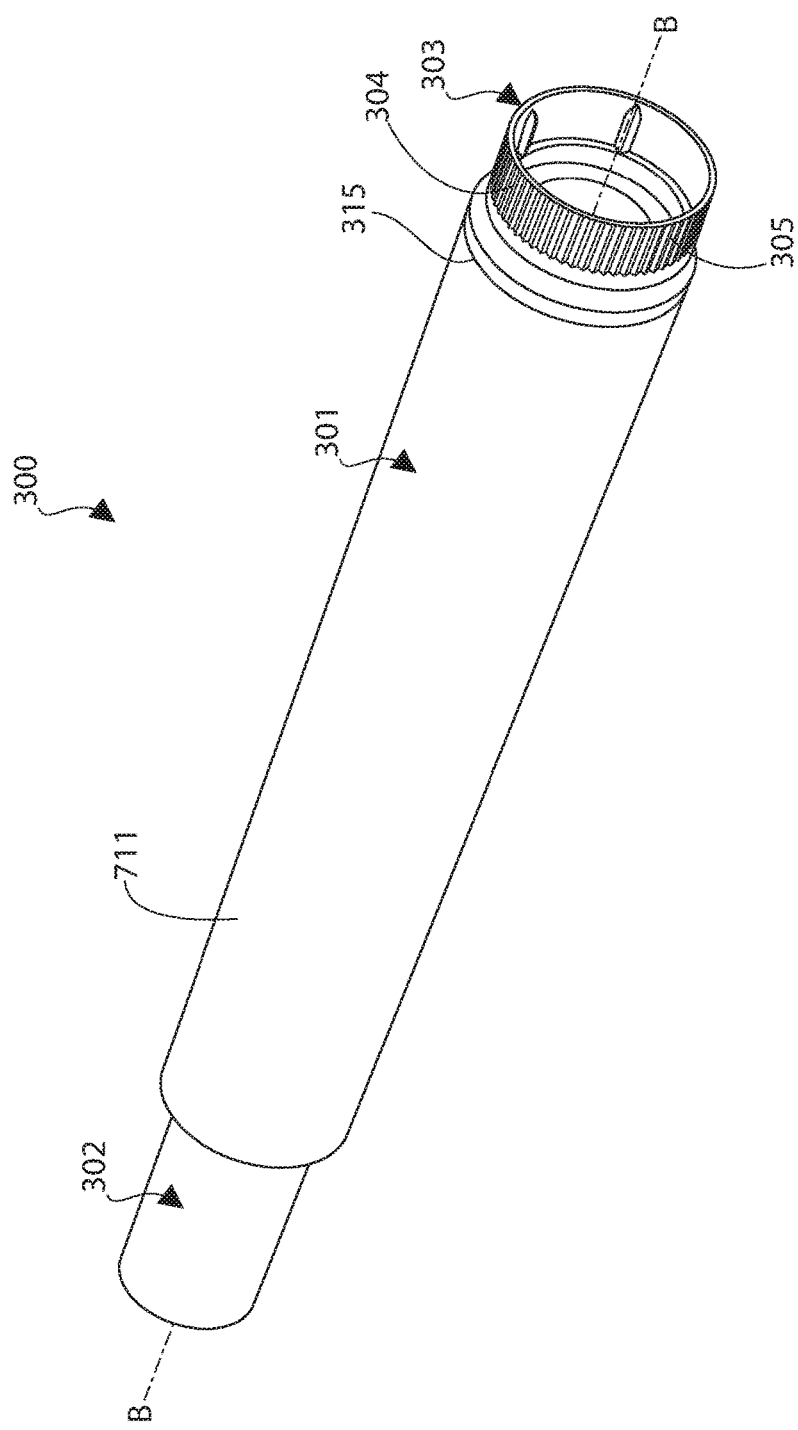
FIG. 3 is a perspective view of the dispenser of the oral care system of FIG. 1.
Figure 4:
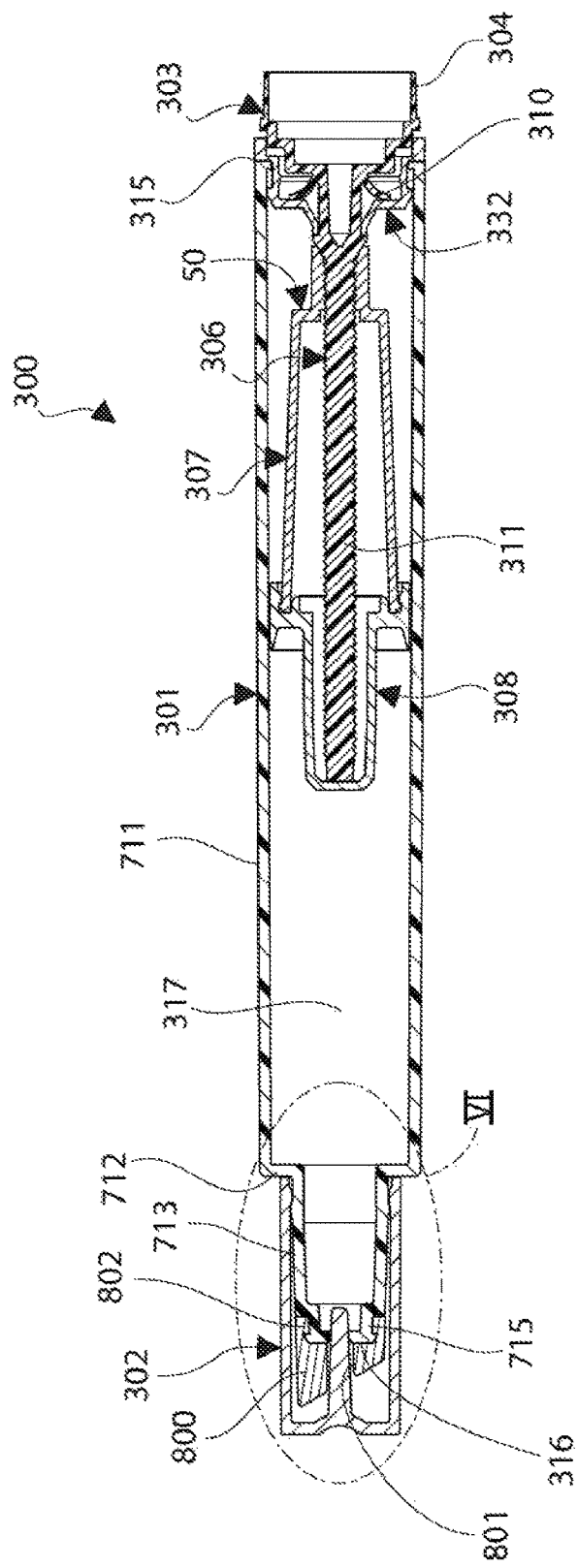
FIG. 4 is a longitudinal cross-sectional view of the dispenser of FIG. 3 taken along the longitudinal axis B-B.
Figure 5:
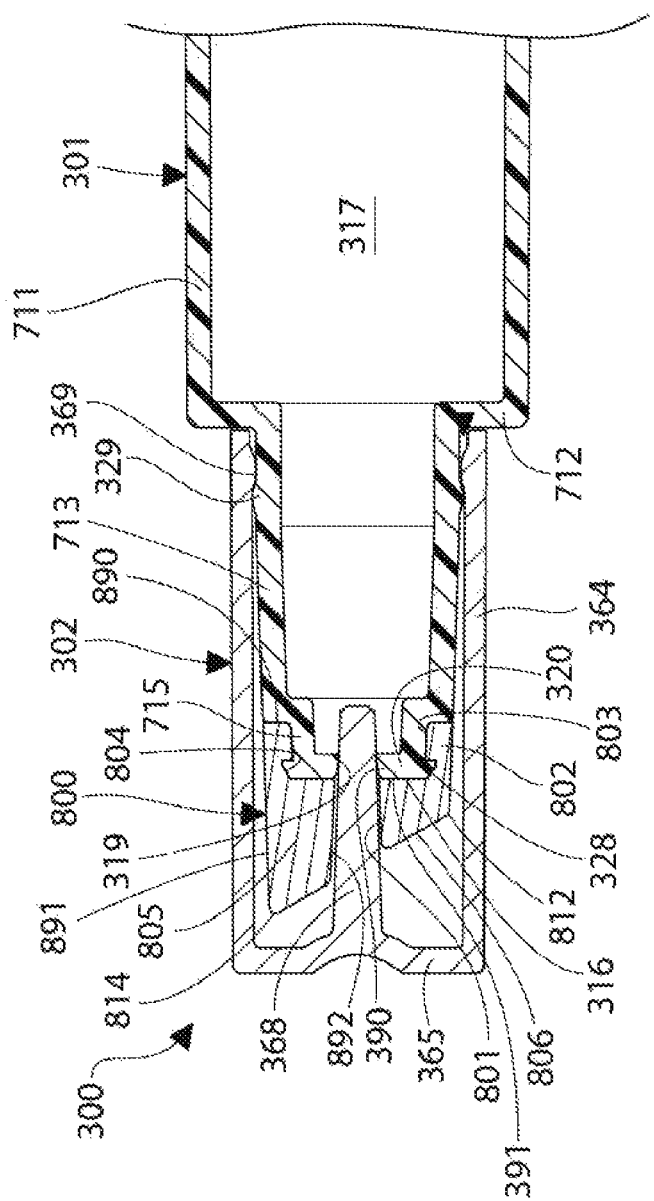
FIG. 5 is a close-up view of area VI of FIG. 4.
Figure 6:
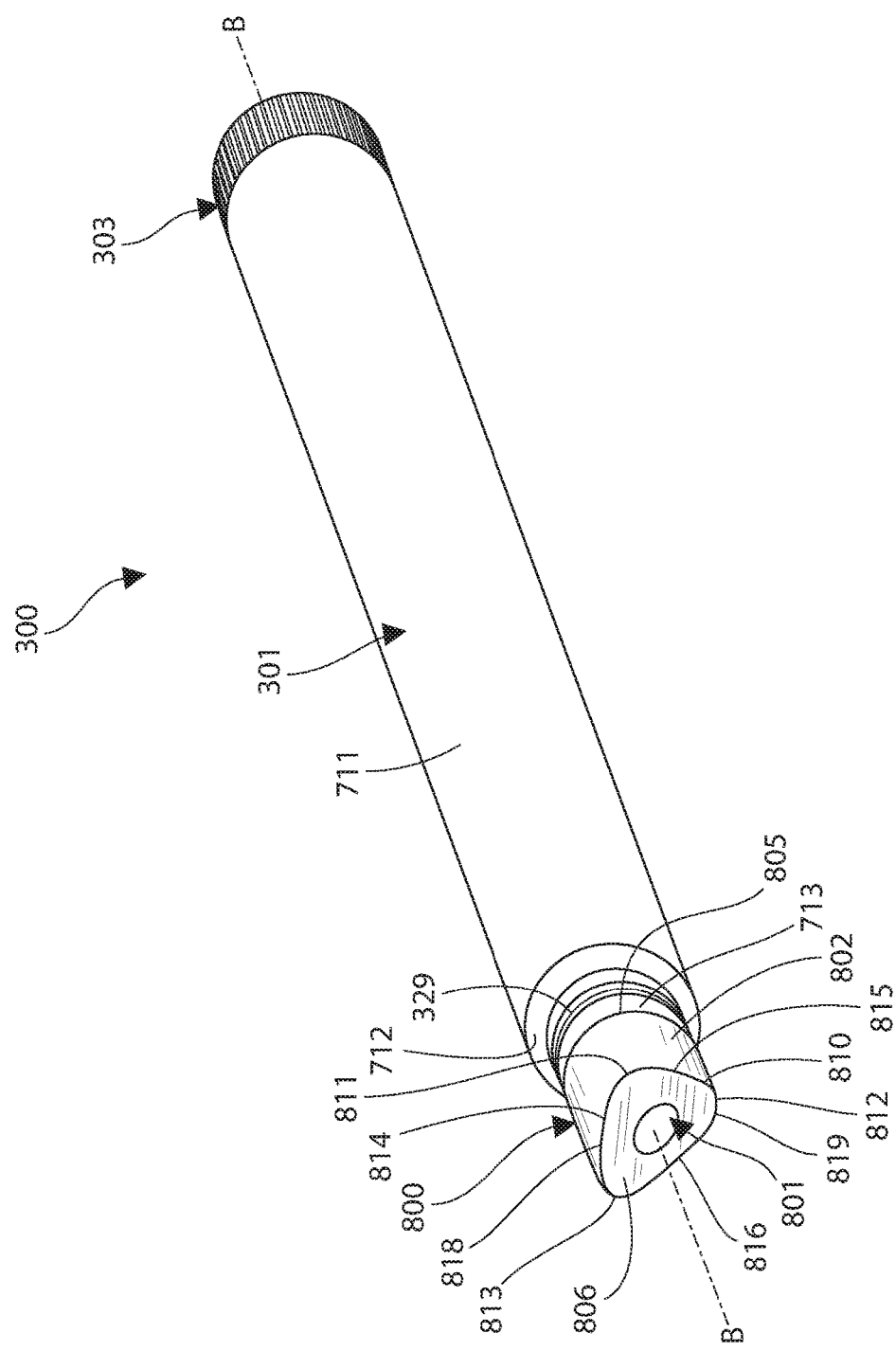
FIG. 6 is a perspective view of the dispenser of FIG. 3 with the cap removed.
Figure 7:
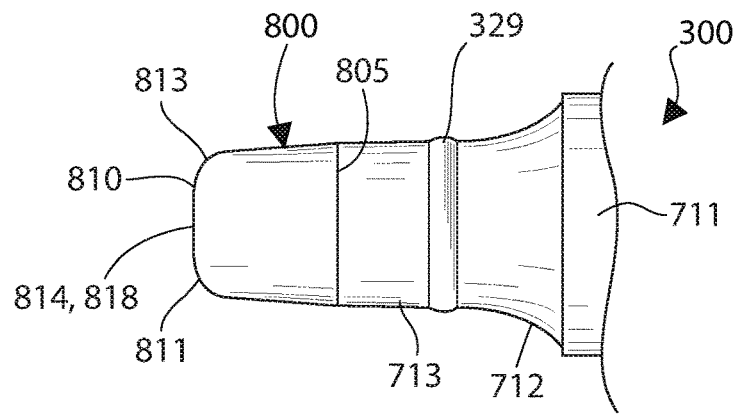
FIG. 7 is a top view of the resilient applicator and distal portion of the housing of the dispenser of FIG. 6.
Figure 8:
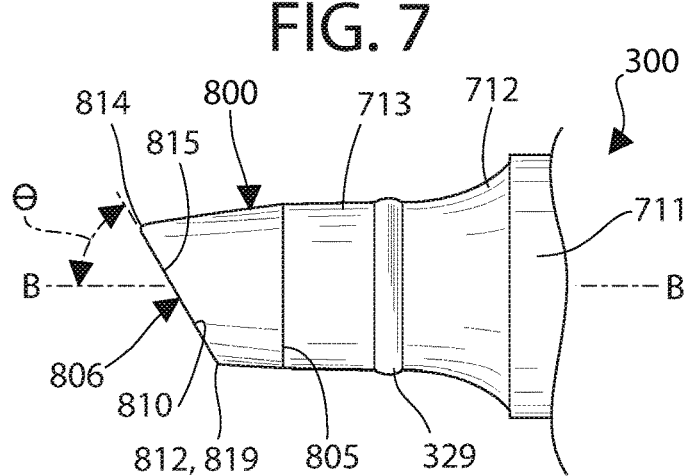
FIG. 8 is a right-side view of the resilient applicator and distal portion of the housing of the dispenser of FIG. 6.
Figure 9:
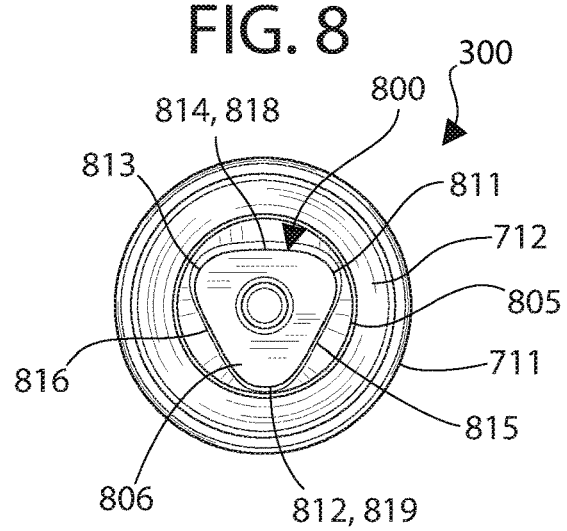
FIG. 9 is a front view of the resilient applicator and distal portion of the housing of the dispenser of FIG. 6.

Referring now to FIGS. 3-5 concurrently, the dispenser 300 is schematically illustrated. The dispenser 300 is an elongated tubular pen-like structure that extends along a longitudinal axis B-B. In the exemplified embodiment, the dispenser 300 generally comprises a housing 301, a resilient applicator 800 coupled to the housing 301, a removable cap 302 coupled to one end of the housing 301 that encloses the resilient applicator 800, and an actuator 303 coupled to the opposite end of the housing 301 (as discussed in detail below the actuator 303 is part of a larger fluid delivery system 50).

The housing 301 is an elongated hollow tubular structure extending along the longitudinal axis B-B from a proximal end 315 to a distal end 316. In the exemplified embodiment, the housing 301 has a generally circular transverse cross-sectional profile. However, the invention is not to be so limited and in certain other embodiments the housing 301 can have a non-circular transverse cross-sectional profile. The housing 301 is in the form of an elongated tubular barrel that extends along a central axis that is coaxial with the longitudinal axis B-B.

The housing 301 generally comprises a product containing portion 711 for containing the fluid therein, an annular shoulder portion 712, and a neck portion 713 extending form the annular shoulder portion 712. The neck portion 713 is narrowed relative to the product containing portion 711. The annular shoulder portion 712 provides a transition structure between the product containing portion 711 and the neck portion 713. The housing 301, and more particularly the product containing portion 711 in the exemplified embodiment, defines an internal reservoir 317 containing the desired fluid or product therein, which can be any active or inactive oral care agent.

The fluid and/or its carrier may be in any form such as a solid or a flowable material including without limitation viscous pastes/gels or less viscous liquid compositions. The fluid is a flowable material having a low viscosity in certain embodiments. Any suitable fluid can be used in the present invention. For example, the fluid may include oral care agents such as whitening agents, including without limitation, peroxide containing tooth whitening compositions. Suitable peroxide containing tooth whitening compositions are disclosed in U.S. patent Ser. No. 11/403,732, filed Apr. 13, 2006, to the present assignee, the entirety of which is hereby incorporated by reference. While a tooth whitening agent and a sensitivity agent are the exemplified active agents in the present invention, any other suitable oral care agents can be used with embodiments of the present invention and, thus, stored within the reservoir 317. Contemplated fluids include oral care agents that can be an active or non-active ingredient, including without limitation, antibacterial agents; oxidative or whitening agents; enamel strengthening or repair agents; tooth erosion preventing agents; anti-sensitivity ingredients; gum health actives; nutritional ingredients; tartar control or anti-stain ingredients; enzymes; sensate ingredients; flavors or flavor ingredients; breath freshening ingredients; oral malodor reducing agents; anti-attachment agents or sealants; diagnostic solutions; occluding agents; anti-inflammatory agents; dry mouth relief ingredients; catalysts to enhance the activity of any of these agents; colorants or aesthetic ingredients; and combinations thereof. The fluid in one embodiment is free of (i.e., is not) toothpaste. Instead, the fluid is intended to provide supplemental oral care benefits in addition to merely brushing one's teeth. Other suitable oral care fluids could include lip balm or other materials that are typically available in a semi-solid state.

In another embodiment, the fluid is a tooth anti-sensitivity agent as the resilient applicator 800 is particularly suited for optimal application of tooth anti-sensitivity agent to the tooth surface. In some embodiments, the materials useful in the oral care fluid contained in the reservoir may include oral care compositions comprising a basic amino acid in free or salt form. In one embodiment, the basic amino acid may be arginine. Various formulations would be useful to supply the arginine to the user. One such oral care composition, e.g., a dentifrice, may be used comprising:
  i. an effective amount of a basic amino acid, in free or salt form, e.g., arginine, e.g., present in an amount of at least about 1%, for example about 1 to about 30%; by weight of total formulation, weight calculated as free base;
  ii. an effective amount of fluoride, e.g., a soluble fluoride salt, e.g., sodium fluoride, stannous fluoride or sodium monofluorophosphate, providing from about 250 to about 25,000 ppm fluoride ions, e.g., about 1,000 to about 1,500 ppm; and
  iii. an abrasive, e.g., silica, calcium carbonate or dicalcium phosphate.

The dental treatment materials of the present invention may have a viscosity suitable for use in tooth treatment applications and methods. As used herein, the "viscosity" shall refer to "dynamic viscosity" and is defined as the ratio of the shearing stress to the rate of deformation as measured by AR 1000-N Rheometer from TA Instruments, New Castle, Del.

When measured at a shear rate of 1 seconds$^{-1}$, the viscosity may have a range with the lower end of the range generally about 0.0025 poise, about 0.1 poise, and more specifically about 75 poise, with the upper end of the range being selected independently of the lower end of the range and generally about 10,000 poise, specifically about 5,000 poise, and more specifically about 1,000 poise. Non-limiting examples of suitable viscosity ranges when measured at a shear rate of 1 seconds$^{-1}$ includes, about 0.0025 poise to about 10,000 poise, about 0.1 poise to about 5,000 poise, about 75 poise to about 1000 poise, and about 0.1 poise to about 10,000 poise.

When measured at a shear rate of 100 seconds$^{-1}$, the viscosity will have a range with the lower end of the range generally about 0.0025 poise, specifically about 0.05 poise, and more specifically about 7.5 poise, with the upper end of the range being selected independently of the lower end of the range and generally about 1,000 poise, specifically about 100 poise, and more specifically about 75 poise. Non-limiting examples of suitable viscosity ranges when measured at a shear rate of 100 seconds$^{-1}$ includes, about 0.0025 poise to about 1,000 poise, about 0.05 poise to about 100 poise, about 7.5 poise to about 75 poise, and about 0.05 poise to about 1,000 poise.

When measured at a shear rate of 10,000 seconds$^{-1}$, the viscosity will have a range with the lower end of the range generally about 0.0025 poise, specifically about 0.05 poise, and more specifically about 5 poise, with the upper end of the range being selected independently of the lower end of the range and generally about 500 poise, specifically about 50 poise. Non-limiting examples of suitable viscosity ranges when measured at a shear rate of 10,000 seconds$^{-1}$ includes, about 0.0025 poise to about 500 poise, about 0.05 poise to about 50 poise, about 5 poise to about 50 poise, and about 0.05 poise to about 500 poise.

The housing 301 is constructed of a material that is sufficiently rigid to provide the necessary structural integrity for the dispenser 300. For example, the housing 301 can be formed of a moldable hard plastic. Suitable hard plastics include polymers and copolymers of ethylene, propylene, butadiene, vinyl compounds and polyesters such as polyethylene terephthalate. The chosen plastic(s), however, should be compatible with the fluid that is to be stored within the dispenser 300 and should not be corroded or degraded by the fluid.

While the housing 301 is exemplified as a single layer construction, in certain embodiments, the housing 301 may be a multi-layer construction. In certain multi-layer embodiments, an inner layer can be formed from the hard plastic materials described immediately above while an outer layer can be formed of a soft resilient material, such as an elastomeric material. Suitable elastomeric materials include thermoplastic elastomers (TPE) or other similar materials used in oral care products. The elastomeric material of the outer layer may have a hardness durometer measurement ranging between A13 to A50 Shore hardness, although materials outside this range may be used. A suitable range of the hardness durometer rating is between A25 to A40 Shore hardness. While an over-molding construction is one suitable method of forming the outer layer, a suitable deformable thermoplastic material, such as TPE, may be formed in a thin layer and attached to inner layer with an appropriate adhesive, sonic welding, or by other means.

The fluid delivery system 50 provides the mechanism by which a user can dispense (or deliver) the fluid that is within the internal reservoir 317 from the dispenser 300. In the exemplified embodiment, the fluid delivery system 50 comprises a reciprocator 306, an extension member 307, an elevator 308, and a collar 332. The reciprocator 306 generally comprises the actuator 303, a resilient member 310 and a drive screw 311. In the exemplified embodiment, the actuator 303, the resilient member 310 and the drive screw 311 are integrally formed to form the reciprocator 306 as a unitary structure. The structural and function details of the fluid delivery system 50 are fully described in the priority application, Patent Cooperation Treaty Patent Application No. PCT/US10/60874, which was filed on Dec. 22, 2010, and is fully incorporated herein by reference. Thus, many of the details of the fluid delivery system 50 will not be discussed herein.

Moreover, many different types of fluid delivery systems can be utilized in the dispenser 300 in accordance with the present invention. For example, the fluid delivery system 50 can be any type of automated or manual system that is capable of delivering the fluid that is within the internal reservoir 317 from the dispenser 300. For example, in certain alternate embodiments, the fluid delivery system 50 can be incorporated into the housing 301 by simply making the housing 301 transversely compressible. In still other alternate embodiments, the fluid delivery system 50 can be an electrical, mechanical or electromechanical pump system. Such pump systems may utilize a piston, pressurization, or combinations thereof.

The rotatable actuator 303 extends from the proximal end 315 of the housing 301. The dispenser 300 is designed so as to be capable of being operated to dispense the fluid stored therein using a single hand by rotating the actuator 303. Specifically, in the exemplified embodiment the dispenser 300 is positioned in a user's hand so that the actuator 303 is lodged in the palm of the user's hand. The user then uses the fingers of that same hand to rotate the housing 301 (while keeping the actuator 303 stationary relative to the housing 301). As a result, the fluid contained therein is dispensed from the dispenser 300.

The actuator 303 protrudes axially from a proximal end of the housing 301 so that a user can easily grip and rotate the actuator 303. A plurality of protuberances 305, in the form of axially aligned and spaced-apart ridges, are formed on an outer surface 304 of the actuator 303 to further facilitate gripping and rotation. The actuator 303 is rotatable with respect to the housing 301. In the exemplified embodiment, the actuator 303 has a substantially circular transverse cross-sectional profile. The actuator 303 is sized and shaped so that its transverse cross-sectional profile fits within the transverse cross-sectional profile of the housing 301. Of course, depending on the fluid delivery system 50 utilized in the dispenser 300, the actuator can be a translation-type actuator, a click-type actuator, a slide actuator, a depressible button, or incorporated into one of the other components, such as the housing 301 as discussed above.

The cap 302 has a transverse cross-sectional profile that corresponds in shape to the transverse cross-sectional profile of the housing 301. In the exemplified embodiment, both the cap 302 and the housing 301 have a circular cross-sectional profile. Of course, non-circular transverse cross-sectional profiles can be utilized to facilitate gripping and/or twisting to remove the cap from the housing so that the fluid can be dispensed from the internal reservoir 317 of the dispenser 300.

A dispensing orifice 319 is provided at the distal end 316 of the housing 301 through which fluid stored in the reservoir 317 is dispensed from the housing 300. The resilient applicator 800 also comprises a dispensing orifice 801. The dispensing orifice 801 of the resilient applicator 800 is aligned with the dispensing orifice 319 of the housing 301 so that the fluid within the internal reservoir 317 can exit the dispenser 300 for application to the desired oral surface of the user upon actuation of the actuator 303. The dispensing orifices 319, 801 are centrally located along the longitudinal axis B-B of the dispenser 300. Of course, in alternate embodiments, the dispensing orifices 319, 801 may be offset partially or entirely from the longitudinal axis B-B.

Referring solely now to FIG. 5, the neck portion 713 of the housing 301 has a reduced transverse cross-sectional area in comparison to the product containing portion 301. The neck portion 713 extends axially from the annular shoulder portion 712 of the housing 301 and provides a structure for coupling the resilient applicator 800 to the housing 300. More specifically, the neck portion 713 comprises a plug portion 715 that can be slid into an internal cavity 803 of a sleeve portion 802 of the resilient applicator 800 to effectuate said coupling. In the exemplified embodiment, the sleeve portion 802 of the resilient applicator 800 has a circular transverse cross-sectional profile. However, the invention is not to be so limited and in certain other embodiments the sleeve portion 802 can have other transverse cross-sectional shapes.

When the dispenser 300 is fully assembled, the plug portion 715 of the housing 301 is disposed and retained within the internal cavity 803 of the sleeve portion 802 of the resilient applicator 800. The retention of the resilient applicator 800 to the housing 300 is enhanced by the mating of a protuberance 328 of the housing 301 with a depression 804 of the resilient applicator 800. More specifically, the plug portion 715 of the housing 301 comprises the protuberance 328, which protrudes from an outer surface of the plug portion 715. Similarly, the sleeve portion 802 of the resilient applicator 800 comprises the depression 804 which is formed into an inner surface of the sleeve portion 802. In the exemplified embodiment, the depression 804 is in the form of an annular groove while the protuberance 328 is in the form of an annular flange. Of course, the depression 804 and the protuberance 328 can take on wide variety of embodiments so long as they are capable of mating with one another when the dispenser 300 is fully assembled to provide a level of axial retention to the resilient applicator 800. For example, the depression 804 can take on the form of one or more dimples, one or more notches, one or more channels, and combinations thereof. Similarly, the protuberance 328 can take on the form of, for example, one or more ridges, one or more barbs, one or more tangs, one or more bumps, and combinations thereof. Furthermore, while the depression 804 is located in the resilient applicator 800 and the protuberance 328 is located on the housing 301 in the exemplified embodiment, in certain alternate embodiments the resilient applicator 800 may include the protuberance 328 while the housing 301 comprises the depression 804. Of course, in certain embodiments the applicator 800 can be integrally formed with the housing 301, or a portion thereof, rather than separately formed and coupled thereto as described herein. Moreover, in other embodiment, the protuberance 328 and depression 804 may be omitted all together.

The resilient applicator 800 generally comprises a main body portion 805 and the sleeve portion 802. The main body portion 805 has a working surface 806 and a bottom surface 890. The bottom surface 890 of the main body portion 805 is in contact with the top surface 391 of the transverse end wall 390 of the housing 301. The main body portion 805 further comprises an outer peripheral surface 891 and an inner surface 892, the inner surface 892 defining the dispensing orifice 801. The dispensing orifice 801 of the resilient applicator forms a fluid passageway from the working surface 806 of the resilient applicator 800 to the dispensing orifice 319 of the housing 301, thereby forming a passageway through which fluid contained within the internal reservoir 317 can be dispensed from the dispenser 300 to the desired oral surface. The fluid passageway has a transverse cross-sectional area that tapers from the working surface 806 to the bottom surface 890. Furthermore, the main body portion 805 has a thickness measured from the outer peripheral surface 891 to the inner surface 892 along a reference plane that is substantially perpendicular to the longitudinal axis A-A and the dispensing orifice 801 has a width measured along the reference plane. The thickness of the main body portion 805 taken along the reference plane is greater than the width of the dispensing orifice 801 taken along the reference plane.

The removable cap 302 comprises a tubular sidewall 364 and a transverse end wall 365. The removable cap 302 has a closed top end and open bottom end. An axial plug 368 extends axially from a bottom surface of the end wall 365. The removable cap 302 is coupled to the housing 301 by being slid over the resilient applicator 800 and the neck portion 713 of the housing 301. As discussed above, interference between the protuberance 369 of the removable cap 302 and the protuberance 329 of the housing 301 secures the removable cap 302 to the housing 301. When the removable cap 302 is fully assembled to the housing 301, the axial plug 368 extends through and seals the dispensing orifice 801 of the applicator and the dispensing orifice 319 of the housing 301, thereby preventing leaking and/or drying out of the fluid in the reservoir 317.

Referring now to FIGS. 5-9 concurrently, the details of the resilient applicator 800 will be discussed. In the exemplified embodiment, the applicator 800 is formed of unitary mass of resilient material. Suitable resilient materials include, without limitation, natural or synthetic rubbers, thermoplastic elastomers (TPE), and combinations thereof. In one embodiment, the resilient material of the applicator 800 may be a TPE having a Shore A Hardness of 20 to 60, although resilient materials outside this range may be used. In one specific embodiment, the resilient material of the applicator 800 may be a TPE having a Shore A Hardness of 25 to 35.

The resilient applicator 800 generally comprises a main body portion 805 and the sleeve portion 802. The dispensing orifice 801 of the resilient applicator forms a fluid passageway from a working surface 806 of the resilient applicator 800 to the dispensing orifice 319 of the housing 301, thereby forming a passageway through which fluid contained within the internal reservoir 317 can be dispensed from the dispenser 300 to the desired oral surface.

The resilient applicator 800 extends axially from a proximal annular edge 807 and comprises the working surface 806. During use of the dispenser 300, the working surface 806 contacts the oral surface, such as the teeth, to apply the fluid being dispensed from the dispensing orifice 801. In the exemplified, the dispensing orifice 801 is positioned along the longitudinal axis B-B and in a central portion of the working surface 360.

The working surface 806 of the applicator 800 is oriented at an oblique angle Θ to the longitudinal axis B-B of the housing 301. The oblique angle Θ is in a range of 10° to 89°, and more preferably in a range of 25° to 35°. In the exemplified embodiment, the working surface 360 is a substantially planar surface. However, in certain other embodiments the working surface can be contoured. Moreover, while the working surface 806 is exemplified as a substantially smooth surface, the working surface 806 may include protuberances and/or depressions (or otherwise be given an uneven topography) in alternate embodiments, such as those disclosed in FIGS. 10-12.

The working surface 806 is defined by a polygonal perimeter edge 810 comprising a plurality of apex portion 811-813 and a plurality of side portions 814-816. Thought of another way, the working surface 360 is defined by a multi-lobed perimeter edge 810 comprising a plurality of lobes 811-813 and a plurality of side portions 814-816. For purposes of further discussion herein, the details of the perimeter edge 810 of the resilient applicator 800 will be described in terms of a polygonal shape having apex portions with the understanding that the aforementioned lobe terminology can be used interchangeably as appropriate.

Each of the side portions 814-816 extend between a pair of the adjacent apex portion 811-813. Specifically, in the exemplified embodiment, the side portion 814 extends between apex portions 811, 813, the side portion 815 extends between apex portions 811, 812, and the side portion 816 extends between apex portions 812, 813.

In the exemplified embodiment, the polygonal perimeter edge 810 is generally triangular and, thus has three apex portions 811-813 and three side portions 814-816. When the lobe terminology is utilized, the perimeter edge 810, in the exemplified embodiment, is tri-lobed. However, the invention is not to be so limited and the perimeter edge 810 can take the form of other polygonal or multi-lobed shapes as desired.

In the exemplified embodiment, each of the apex portions 811-813 are rounded, thereby having a first radius curvature. In one embodiment, the first radius of curvature is in a range of 0.5 mm to 3.5 mm, and more preferably 1.9 mm to 2.2 mm. However, in alternate embodiments, a subset or all of the apex portions 811-813 can come to a point rather than being rounded.

In the exemplified embodiment, each of the side portions 814-816 is substantially linear/straight. However, in certain other embodiments, one or more of the side portions 814-816 can be slightly curved or otherwise slightly contoured along a portion or all of their length. However, in embodiments where the side portions 814-816 are curved, the side portions 814-816 will have a second radius of curvature that is substantially greater than the first radius of curvature of each of the apex portions 811-813 so that a clear visible distinction between the apex portions 811-813 and the side portions 814-816 is present. In one such embodiment, the ratio of the second radius of curvature to the first radius of curvature is in a range of 15.0 mm to 10.0 mm, and more preferably 12.5 mm to 13.5 mm.

By forming the side portions 814-816 to be straight or slightly curved (in comparison to the apex portions), the side portions 814-816 are particularly suited for spreading the fluid that is dispensed from the dispensing orifice 801 along the oral surface.

As mentioned above, the working surface 360 of the applicator 800 is oriented at the oblique angle Θ relative to the longitudinal axis B-B of the housing 301. The angular orientation of the polygonal perimeter 810 about the longitudinal axis B-B is coordinated with the oblique angle Θ so that one of the side portions 814-816 forms a distal-most portion 818 of the resilient applicator 800 (measured along the longitudinal axis B-B). In the exemplified embodiment, it is the side portion 814 that forms the distal-most portion 818 of the resilient applicator 800. In the exemplified embodiment, the side portion 814 of the polygonal perimeter edge 810 that forms the distal-most portion 818 of the resilient applicator 800 lies entirely within a plane that is substantially normal to the longitudinal axis B-B and intersects no other portion of the resilient applicator 800 or the housing 301. The invention, however, is not to be limited as such in all embodiments.

In certain embodiments, the angular orientation of the polygonal perimeter 810 about the longitudinal axis B-B is coordinated with the oblique angle Θ so that one of the apex portions 811-813 forms a proximal-most portion 819 of the working surface 806. In the exemplified embodiment, it is the apex portion 812 that forms the proximal-most portion 819 of the working surface 806.

By designing the resilient applicator 800 so that the working surface 806 is angled and oriented as discussed above, the side portion 814, which forms the distal-most portion 818 of the resilient applicator 800, functions in a manner similar to a spatula or trowel and facilitates spreading the fluid onto (and potentially into) the desired oral surface, such as the teeth which have tubules. Moreover, the compressible nature of the resilient material of the resilient applicator 800 further facilitates optimal application as the side portion 814 can take on the contour of the desired oral surface. This can be especially useful and effective for the application of tooth anti-sensitivity agents.

As noted above, the resilient applicator 800 comprises a sleeve portion 802 having a circular transverse cross-sectional profile despite the working surface 806 having a polygonal shape. The circular transverse cross-sectional profile of the sleeve portion 802 facilitates coupling of the resilient applicator 800 to the housing 301 while still affording the advantages discussed above for the working surface 806.

Figure 10:
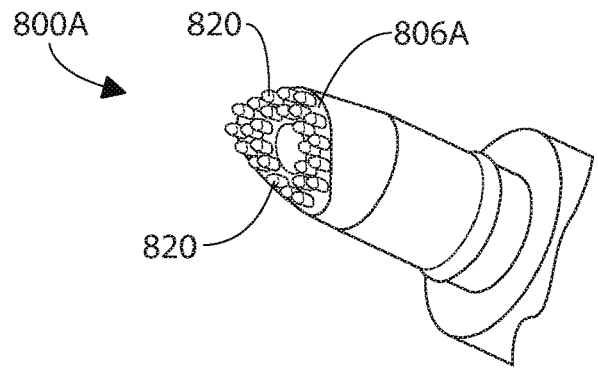
FIG. 10 is a perspective view of a resilient applicator and distal portion of a dispenser according to a second embodiment of the present invention.
Figure 11:
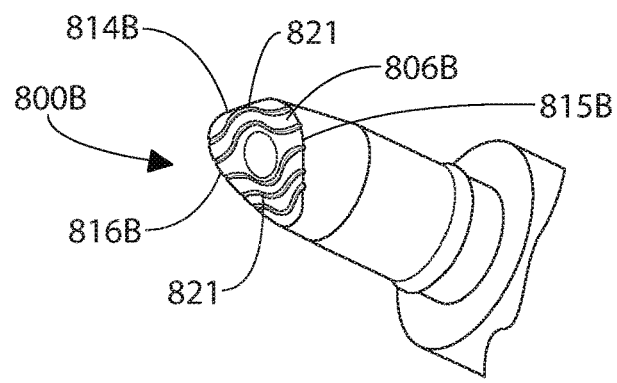
FIG. 11 is a perspective view of a resilient applicator and distal portion of a dispenser according to a third embodiment of the present invention.
Figure 12:
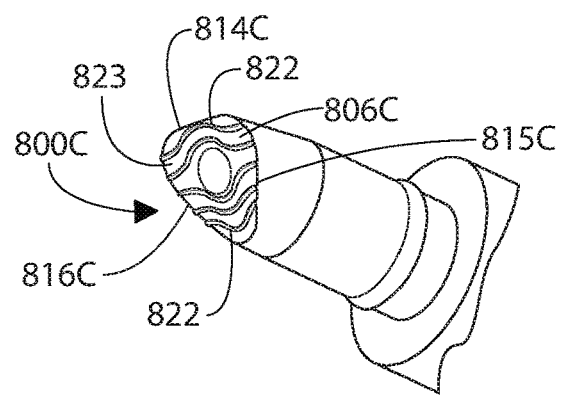
FIG. 12 is a perspective view of a resilient applicator and distal portion of a dispenser according to a fourth embodiment of the present invention.

Referring now to FIGS. 10-12, alternate embodiments of the resilient applicator 800 are illustrated. Referring first to FIG. 10, an applicator 800A is illustrated having a working surface 806A. The working surface 806A comprises a plurality of nubs or protuberances 820 extending outwardly therefrom. The nubs 820 are formed of a resilient material, such as a thermoplastic elastomer, and can be formed integrally with or separately from the resilient applicator 800. Although the exemplified embodiment illustrates a plurality of nubs 820, in other embodiments the working surface 806A may comprise a single nub. Furthermore, the nubs can have a short length or extension from the working surface 806A of approximately 1-3 mm or a greater length of approximately 3-5 mm. A shorter nub will provide a more rigid feel to a user and a longer nub will be able to penetrate deeper within any crevices between or within the teeth, gums and other oral care surfaces. The nubs 820 can provide a massaging effect as the working surface 806A is rubbed against a user's tooth and gum surfaces. Furthermore, the nubs 820 can extend between crevices of the teeth, gums and other oral surfaces for ensuring adequate coverage with the fluid by the applicator 800A.

Referring now to FIG. 11, an applicator 800B is illustrated having a working surface 806B. The working surface 806B comprises a plurality of depressions in the form of elongated grooves 821 provided therein that extend from one of the side portions 815B to an opposing one of the side portions 816B. In the exemplified embodiment, the working surface 806B comprises five grooves 821. However, the invention is not to be so limited and there can be just a single groove or any other number of grooves 821 as will properly fit on the working surface 806B. The grooves 821 provide a channel for the fluid to flow into while it is being dispensed from the dispenser 300. The grooves 821 will enhance the application of the fluid onto any rough surfaces or surfaces that have bumps thereon.

Referring to FIG. 12, an applicator 800C is illustrated having a working surface 806C. The working surface 806C comprises a plurality of ridges 822 that extend from one of the side portions 815C to an opposing one of the side portions 816C. The ridges 822 are formed of a resilient material, such as a thermoplastic elastomer, and can be formed integrally with or separately from the resilient applicator 800. Furthermore, in this embodiment channels 823 are formed between adjacent ones of the ridges 822. This embodiment will further enhance and facilitate application of the fluid onto the tooth, gum and other oral surfaces.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

While the foregoing description and drawings represent the exemplary embodiments of the present invention, it will be understood that various additions, modifications and substitutions may be made therein without departing from the spirit and scope of the present invention as defined in the accompanying claims. In particular, it will be clear to those skilled in the art that the present invention may be embodied in other specific forms, structures, arrangements, proportions, sizes, and with other elements, materials, and components, without departing from the spirit or essential characteristics thereof. One skilled in the art will appreciate that the invention may be used with many modifications of structure, arrangement, proportions, sizes, materials, and components and otherwise, used in the practice of the invention, which are particularly adapted to specific environments and operative requirements without departing from the principles of the present invention. The presently disclosed embodiments are therefore to be considered in all respects as illustrative and not restrictive, the scope of the invention being defined by the appended claims, and not limited to the foregoing description or embodiments.

What is claimed is:

1. A dispenser comprising:
   a housing having an internal reservoir containing a fluid, the housing extending from a proximal end to a distal end along a longitudinal axis, the distal end of the housing comprising a transverse end wall having a top surface;
   a resilient applicator coupled to the distal end of the housing, the resilient applicator comprising a main body portion and a dispensing orifice for dispensing the fluid from the reservoir, the main body portion having a bottom surface that is in contact with the top surface of the transverse end wall of the housing;
   wherein the resilient applicator comprises a working surface that is oriented at an oblique angle to the longitudinal axis of the housing; and
   wherein the working surface of the resilient applicator comprises a polygonal perimeter edge, the polygonal perimeter edge comprising a plurality of apex portions and a plurality of side portions, wherein one of the plurality of side portions forms a distal most-portion of the resilient applicator and one of the plurality of apex portions forms a proximal-most portion of the working surface.

2. The dispenser according to claim 1 wherein the polygonal perimeter edge is generally triangular having three apex portions and three side portions.

3. The dispenser according to claim 1 wherein the plurality of apex portions are rounded.

4. The dispenser according to claim 1 wherein the plurality of side portions are substantially linear.

5. The dispenser according to claim 1 wherein the dispensing orifice is located along the longitudinal axis in a central portion of the working surface.

6. The dispenser according to claim 1 wherein the housing comprises an elongated barrel portion having a central axis that is coaxial with the longitudinal axis, wherein the barrel portion comprises a product containing portion, a shoulder portion, and a neck portion, the resilient applicator coupled to the neck portion.

7. The dispenser according, to claim 1 wherein the resilient applicator comprises a plurality of protuberances extending from the working surface and surrounding the dispensing orifice.

8. A dispenser comprising:
   a housing having an internal reservoir containing a fluid, the housing extending from a proximal end to a distal end along a longitudinal axis;
   a resilient applicator coupled to the distal end of the housing, the resilient applicator comprising a main body portion having a working surface and a bottom surface and a dispensing orifice for dispensing the fluid from the reservoir, the dispensing orifice forming a fluid passageway from the bottom surface to the working surface, the fluid passageway having a transverse cross-sectional area that tapers from the working surface to the bottom surface; and
   wherein the working surface is oriented at an oblique angle to the longitudinal axis of the housing.

9. The dispenser according to claim 8 wherein the working surface comprises a polygonal perimeter edge, the polygonal perimeter edge comprising a plurality of apex portions and a plurality of side portions, wherein one of the plurality of side portions forms a distal most-portion of the resilient applicator.

10. The dispenser according, to claim 9 wherein the plurality of apex portions are rounded and the plurality of side portions are substantially linear, and wherein one of the plurality of apex portions forms a proximal-most portion of the working surface.

11. The dispenser according to claim 8 wherein the dispensing orifice terminates in a circular opening located along the longitudinal axis in a central portion of the working surface.

12. The dispenser according to claim 8 wherein the dispenser comprises a fluid delivery system for delivering the fluid through the dispensing orifice.

13. The dispenser according to claim 8 wherein the working surface of the resilient applicator is substantially planar.

14. The dispenser according to claim 8 further comprising a removable cap coupled to the housing and enclosing the resilient applicator, the removable cap comprising an axial plug that extends through and seals the dispensing orifice of the resilient applicator.

15. The dispenser according to claim 14 wherein a gap exists between the working surface of the resilient applicator and a transverse end wall of the removable cap, a portion of the axial plug located within the gap.

16. The dispenser according to claim 14 wherein the axial plug extends into and through the fluid passageway of the main body portion of the resilient applicator and into and through a dispensing orifice of the housing, a portion of the axial plug protruding from the working surface of the resilient applicator.

17. The dispenser according to claim 8 wherein the transverse cross-sectional area of the fluid passageway decreases from the working surface to the bottom surface.

18. A dispenser comprising:
a housing having an internal reservoir containing a fluid, the housing extending from a proximal end to a distal end along a longitudinal axis; and
an applicator formed of a unitary mass of resilient material and coupled to the distal end of the housing, the applicator comprising a main body portion having an outer peripheral surface and an inner surface that defines a dispensing orifice for dispensing the fluid from the reservoir;
wherein the applicator comprises a working surface that is oriented at an oblique angle to the longitudinal axis of the housing, the working surface defined by a multi-lobed perimeter edge, the multi-lobed perimeter edge comprising a substantially straight side portion extending between each pair of adjacent lobes, one of the substantially straight side portions forming a distal most-portion of the applicator.

19. The dispenser according to claim 18 wherein the multi-lobed perimeter edge is tri-lobed having three of the substantially straight portions, and wherein one of the lobes forms a proximal-most portion of the working surface.

20. The dispenser according to claim 17 wherein the transverse cross-sectional area of the fluid passageway decreases with a constant slope from the working surface to the bottom surface.

* * * * *